US009340909B2

(12) United States Patent
Mitsuno

(10) Patent No.: US 9,340,909 B2
(45) Date of Patent: May 17, 2016

(54) NONWOVEN FABRIC, ABSORBENT ARTICLE COMPRISING THE SAME, AND METHOD OF FORMING THE SAME

(75) Inventor: Satoshi Mitsuno, Kagawa (JP)

(73) Assignee: Unicharm Corporation, Ehime (JP)

( * ) Notice: Subject to any disclaimer, the term of this patent is extended or adjusted under 35 U.S.C. 154(b) by 136 days.

(21) Appl. No.: 13/824,508

(22) PCT Filed: Sep. 30, 2011

(86) PCT No.: PCT/JP2011/073162
§ 371 (c)(1),
(2), (4) Date: Mar. 18, 2013

(87) PCT Pub. No.: WO2012/043892
PCT Pub. Date: Apr. 5, 2012

(65) Prior Publication Data
US 2013/0280481 A1 Oct. 24, 2013

(30) Foreign Application Priority Data

Sep. 30, 2010 (JP) ................................. 2010-222335

(51) Int. Cl.
*B32B 3/24* (2006.01)
*D04H 3/018* (2012.01)
(Continued)

(52) U.S. Cl.
CPC .............. *D04H 3/018* (2013.01); *A61F 13/513* (2013.01); *A61F 13/51104* (2013.01); *A61F 13/51108* (2013.01); *A61F 13/51121* (2013.01); *D02J 3/02* (2013.01); *D04H 3/11* (2013.01);
(Continued)

(58) Field of Classification Search
CPC ......................... Y10T 428/24826; D04H 3/018
USPC ........................................... 428/198
See application file for complete search history.

(56) References Cited

U.S. PATENT DOCUMENTS 4,333,979 A * 6/1982 Sciaraffa et al. .............. 428/179
4,960,630 A 10/1990 Greenway et al.
(Continued)

FOREIGN PATENT DOCUMENTS

CN 103124813 A 5/2013
EP 2 559 794 A1 2/2013
(Continued)

OTHER PUBLICATIONS

International Search Report from corresponding PCT application No. PCT/JP2011/073162 dated Dec. 13, 2011 (3 pgs).
(Continued)

*Primary Examiner* — William P Watkins, III
(74) *Attorney, Agent, or Firm* — Brinks Gilson & Lione

(57) ABSTRACT

A nonwoven fabric that is easily deformed but resistant to collapse, and that has excellent air permeability in the planar direction. The nonwoven fabric comprises continuous fibers and bonded sections formed by bonding multiple fibers including the continuous fibers, wherein the nonwoven fabric comprises a first side and a second side on the side opposite the first side, the first side comprises a plurality of projections, each projection including at least one bonded section, a plurality of projections including no bonded section, and at least one recess, the second side comprises a plurality of recesses, each recess overlapping with at least a part of the projection of the first side, and the coefficient of variation of the diameters of the continuous fibers is at least 10%.

5 Claims, 5 Drawing Sheets

(51) Int. Cl.
  *A61F 13/511* (2006.01)
  *A61F 13/513* (2006.01)
  *D04H 3/11* (2012.01)
  *D04H 3/14* (2012.01)
  *D04H 3/16* (2006.01)
  *D04H 5/03* (2012.01)
  *D04H 5/06* (2006.01)
  *D04H 5/08* (2012.01)
  *D02J 3/02* (2006.01)
  *D06C 23/04* (2006.01)
  *D06C 29/00* (2006.01)

(52) U.S. Cl.
  CPC  *D04H 3/14* (2013.01); *D04H 3/16* (2013.01); *D04H 5/03* (2013.01); *D04H 5/06* (2013.01); *D04H 5/08* (2013.01); *D06C 23/04* (2013.01); *D06C 29/005* (2013.01); *Y10T 428/2481* (2015.01); *Y10T 428/24273* (2015.01); *Y10T 428/24479* (2015.01); *Y10T 428/24612* (2015.01); *Y10T 428/24826* (2015.01)

(56) References Cited

U.S. PATENT DOCUMENTS

| | | | |
|---|---|---|---|
| 5,274,893 A | 1/1994 | Kitamura et al. | |
| 6,551,436 B1 * | 4/2003 | Flohr et al. | 156/251 |
| 2004/0214498 A1 * | 10/2004 | Webb et al. | 442/329 |
| 2010/0065984 A1 | 3/2010 | Akiki et al. | |
| 2013/0172842 A1 | 7/2013 | Mitsuno et al. | |

FOREIGN PATENT DOCUMENTS

| | | |
|---|---|---|
| EP | 2 559 795 A1 | 2/2013 |
| JP | 4-502788 | 5/1992 |
| JP | 4-327255 | 11/1992 |
| JP | 2002-249965 | 6/2002 |
| JP | 2002-249965 A | 9/2002 |
| JP | 2003-073967 | 3/2003 |
| JP | 2003-073967 A | 3/2003 |
| JP | 2004-76178 A | 3/2004 |
| JP | 2006-141838 A | 6/2006 |
| JP | 2009-000173 | 1/2009 |
| JP | 2009-000173 A | 1/2009 |
| JP | 2009-62650 A | 3/2009 |
| JP | 200962650 A | 3/2009 |
| JP | 2009-155741 A | 7/2009 |
| JP | 2010-5925 A | 1/2010 |
| JP | 2010-94535 A | 4/2010 |
| WO | WO 2008/078533 A1 | 7/2008 |
| WO | WO 2011/129463 A1 | 10/2011 |
| WO | WO 2012/043779 A1 | 4/2012 |

OTHER PUBLICATIONS

International Search Report from corresponding PCT application No. PCT/JP2011/073162 dated Dec. 13, 2011 (2 pgs).

European extended Search Report from corresponding European application No. 11829441.2 dated Jul. 27, 2015 (9 pgs).

* cited by examiner

NONWOVEN FABRIC, ABSORBENT ARTICLE COMPRISING THE SAME, AND METHOD OF FORMING THE SAME

RELATED APPLICATION

This application is a 35 U.S.C. §371 national phase filing of International Patent Application No. PCT/JP2011/073162, filed Sep. 30, 2011, through which and to which priority is claimed under 35 U.S.C. §119 to Japanese Patent Application No. 2010-222335, filed Sep. 30, 2010.

TECHNICAL FIELD

The present disclosure relates to a nonwoven fabric, an absorbent article comprising the nonwoven fabric, and a method of forming a nonwoven fabric.

BACKGROUND ART

Nonwoven fabrics are used in absorbent articles such as sanitary products and disposable diapers, cleaning products such as wipers, and medical goods such as masks. However, the nonwoven fabrics used in such products usually have specialized functions according to the purpose of the products and their location of use.

With absorbent articles, for example, it is necessary to employ nonwoven fabrics that expand and contract in response to bodily movement during wear or use, without creating an uncomfortable feeling for the user. Disposable diapers and sanitary napkins require nonwoven fabrics with high elasticity and strength sufficient to prevent tearing during extension, as well as satisfactory feel on the skin, air permeability and liquid-permeability.

Nonwoven fabrics exhibiting the desired performance in such products are usually designed and produced for each individual product. It is therefore considered preferable, from the viewpoint of production cost and environmental protection, for nonwoven fabrics exhibiting desired performance to be more easily formed by modifying certain nonwoven fabrics such as commercially available nonwoven fabrics, and especially relatively low-cost spunbond nonwoven fabrics, meltblown nonwoven fabrics and the like.

As a method of forming a nonwoven fabric suitable for use in an absorbent article comprising a nonwoven fabric as the starting material, PTL 1 discloses a nonwoven fabric having alternating ridges and furrows each extending in one direction, with openings in the furrows, wherein the ridges have a substantially greater fiber content than the furrows, and the fiber density differs between the tops of the ridges and the edges of the openings. In paragraph [0049] of PTL 1, it is stated that an air-through nonwoven fabric or the like may be used as the starting material for the nonwoven fabric, and that it is preferred to employ a water stream or water vapor stream when using a fiber aggregate having bonds at the fiber nodes, as in an air-through nonwoven fabric.

CITATION LIST

Patent Literature

PTL 1 Japanese Unexamined Patent Publication No. 2009-62650

SUMMARY OF INVENTION

Technical Problem

However, when an air-through nonwoven fabric, for example, is used as the starting material for the invention described in PTL 1, it is necessary to increase the energy and temperature for fluid treatment to form ridges, furrows and open holes, because the fibers of the nonwoven fabric are fixed and not easily moved. Yet, increasing the energy and temperature for fluid treatment results in fusion of the fibers in the nonwoven fabric, causing the formed ridges and furrows to be hard. As a result, a nonwoven fabric formed from an air-through nonwoven fabric as described in PTL 1 can potentially be a nonwoven fabric with resistance to deformation by external force, which can sometimes hurt the skin when it is used in sections that directly contact the skin and are subjected to body pressure.

Furthermore, when it is attempted to modify a spunbond nonwoven fabric, meltblown nonwoven fabric or the like as a nonwoven fabric having firmly bonded fibers, paper-thinness and low cushion feel by embossing, as described in PTL 1, it is difficult to form distinct irregularities in the nonwoven fabric, and therefore the sheet as a whole collapses during compression, for example, particularly resulting in inferior air permeability in the planar direction. In addition, when it is attempted to modify a spunbond nonwoven fabric, meltblown nonwoven fabric or the like so that it has distinct irregular shapes, as described in PTL 1, it becomes necessary to increase the fluid energy, and especially the flow rate and temperature, but raising the temperature causes melting of the fibers and fusion between the fibers, forming a hard nonwoven fabric with numerous rough sections, while also increasing production cost.

It is therefore an object of the present disclosure to provide a nonwoven fabric that is easily deformed but resistant to collapse, and that has excellent air permeability in the planar direction.

Solution to Problem

As a result of diligent research directed toward solving the problems described above, the present inventors have completed this disclosure upon finding that the problems mentioned above can be solved by a nonwoven fabric comprising continuous fibers and bonded sections formed by bonding multiple fibers including the continuous fibers, wherein the nonwoven fabric comprises a first side and a second side on the side opposite the first side, the first side comprises a plurality of projections ($V_{11}$), each projection ($V_{11}$) including at least one bonded section, a plurality of projections ($V_{12}$) including no bonded section, and at least one recess ($C_{11}$), the second side comprises a plurality of recesses ($C_{21}$), each recess ($C_{21}$) overlapping with at least a part of the projection ($V_{11}$) of the first side, and the coefficient of variation of the diameters of the continuous fibers is at least 10%.

Advantageous Effects of Invention

The nonwoven fabric of the disclosure has a coefficient of variation of at least 10% for the diameters of the continuous fibers, and therefore the ease of deformation upon application of force differs depending on the individual continuous fibers, so that the nonwoven fabric as a whole has a property whereby it is easily deformed but resistant to collapse.

Furthermore, since the first side of the nonwoven fabric of the disclosure comprises a plurality of projections ($V_{11}$), each projection ($V_{11}$) including at least one bonded section and a plurality of projections ($V_{12}$) including no bonded section, while the second side comprises a plurality of recesses ($C_{21}$), each recess ($C_{21}$) overlapping with at least a part of the projection ($V_{11}$) including the bonded sections of the first side, it has a property whereby it is easily deformed but resistant to collapse.

In addition, the nonwoven fabric of the disclosure has excellent air permeability in the planar direction since it comprises irregularities on the first side.

DESCRIPTION OF EMBODIMENTS

The nonwoven fabric of the disclosure, an absorbent article comprising the nonwoven fabric, and the method of forming a nonwoven fabric, will now be explained in detail.

[Nonwoven Fabric of the Invention]

The nonwoven fabric of the disclosure is a nonwoven fabric comprising continuous fibers and bonded sections formed by bonding multiple fibers including the continuous fibers. The nonwoven fabric of the disclosure comprises a first side and a second side on the side opposite the first side, the first side comprising a plurality of projections ($V_{11}$), each projection ($V_{11}$) including at least one bonded section, a plurality of projections ($V_{12}$) including no bonded section, and at least one recess ($C_{11}$), the second side comprising a plurality of recesses ($C_{21}$), each recess ($C_{21}$) overlapping with at least a part of the projections ($V_{11}$) of the first side, and the coefficient of variation of the diameters of the continuous fibers being at least 10% (this will hereunder be referred to as "specific form and specific coefficient of variation").

Figure 1:
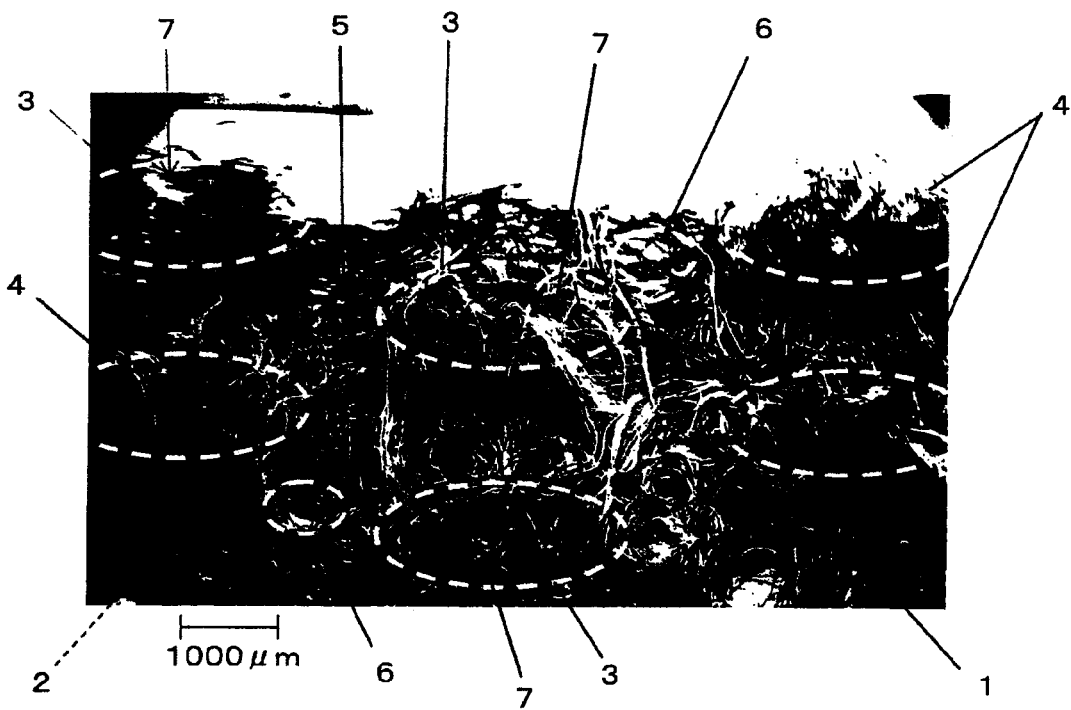
FIG. 1 is a scanning electron micrograph of an embodiment of a nonwoven fabric of the invention.

FIG. 1 is a scanning electron micrograph of an embodiment of a nonwoven fabric of the invention. The nonwoven fabric shown in FIG. 1 is photographed from an oblique top angle on the first side 1. The side opposite the first side 1 is the second side 2. The nonwoven fabric shown in FIG. 1 comprises a plurality of projections ($V_{11}$) 3, each projection ($V_{11}$) including at least one bonded section, a plurality of projections ($V_{12}$) 4 including no bonded section, and at least one recess ($C_{11}$) 5. While not shown here, the second side 2 comprises a plurality of recesses ($C_{21}$) 8, each recess ($C_{21}$) 8 overlapping with at least a part of the projection ($V_{11}$) 3 of the first side 1. In the nonwoven fabric shown in FIG. 1, the projections ($V_{11}$) 3, each projection ($V_{11}$) including at least one bonded section, include at least one bonded section 7.

The nonwoven fabric shown in FIG. 1 also includes a plurality of open holes 6. The open holes 6 are formed by the second side 2 further comprising a plurality of recesses ($C_{22}$) (not shown), and connection being formed between the recesses ($C_{11}$) of the first side and the recesses ($C_{22}$) of the second side. Formation of the open holes greatly improves the air permeability and liquid permeability in the thickness direction of the nonwoven fabric. Thus, when the nonwoven fabric is used in the top sheet of an absorbent article, absorbed liquids can rapidly migrate to the absorbent core through the open holes.

Although the nonwoven fabric shown in FIG. 1 includes open holes, in accordance with further embodiment of the present invention, the open holes may be absent.

Figure 2:
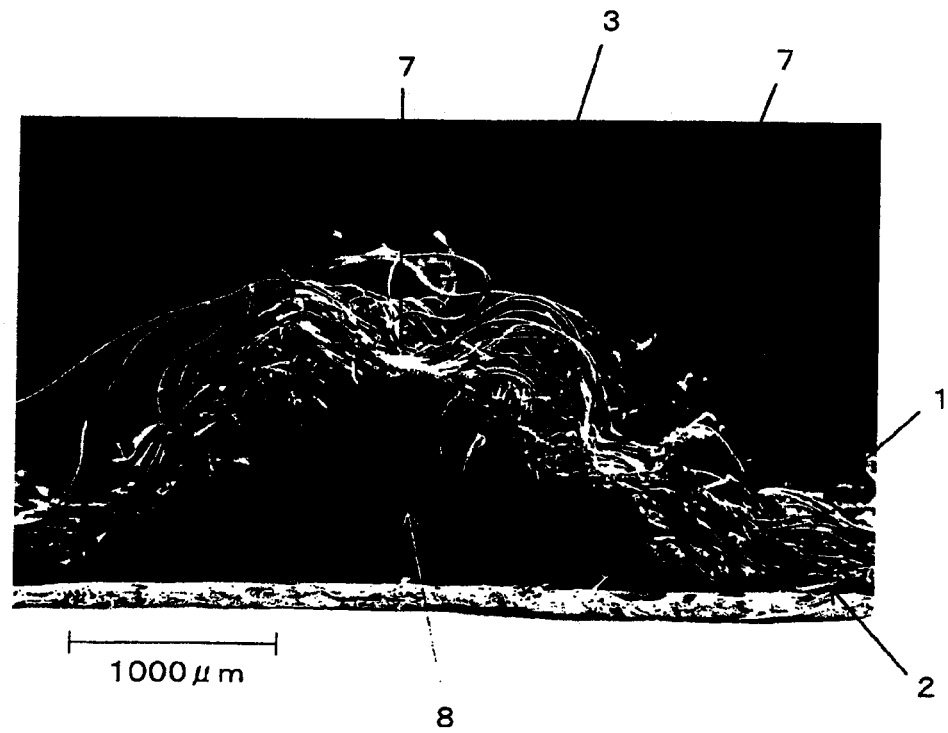
FIG. 2 is a scanning electron micrograph of the cross-section of a projection ($V_{11}$) 3, including a bonded section.

FIG. 2 is a scanning electron micrograph of the cross-section of a projection ($V_{11}$) 3 which includes a bonded section. In FIG. 2, the top side is the first side 1 and the bottom side is the second side 2. The projection ($V_{11}$) 3 shown in FIG. 2 includes 2 bonded sections 7. Also in FIG. 2, the second side 2 comprises the recess ($C_{21}$) 8 overlapping with at least a part of the projection ($V_{11}$) 3 of the first side 1.

As used herein, the term "overlap" as used in relation to the recesses and projections means that the projections and recesses have roughly identical three-dimensional shapes and that the top parts of the projections and the bottom parts of the recesses are separated in the thickness direction of the nonwoven fabric but have roughly identical locations in the planar direction. Therefore, as used herein, the recesses and projections, having roughly identical shapes but wherein the top parts of the projections and the bottom parts of the recesses do not have roughly identical locations in the planar direction, are not included in the concept of "overlapping".

Incidentally, the "top parts of the projections" are the highest locations of the projections in the thickness direction, and the "bottom parts of the recesses" are the lowest locations of the recesses in the thickness direction.

Figure 3:
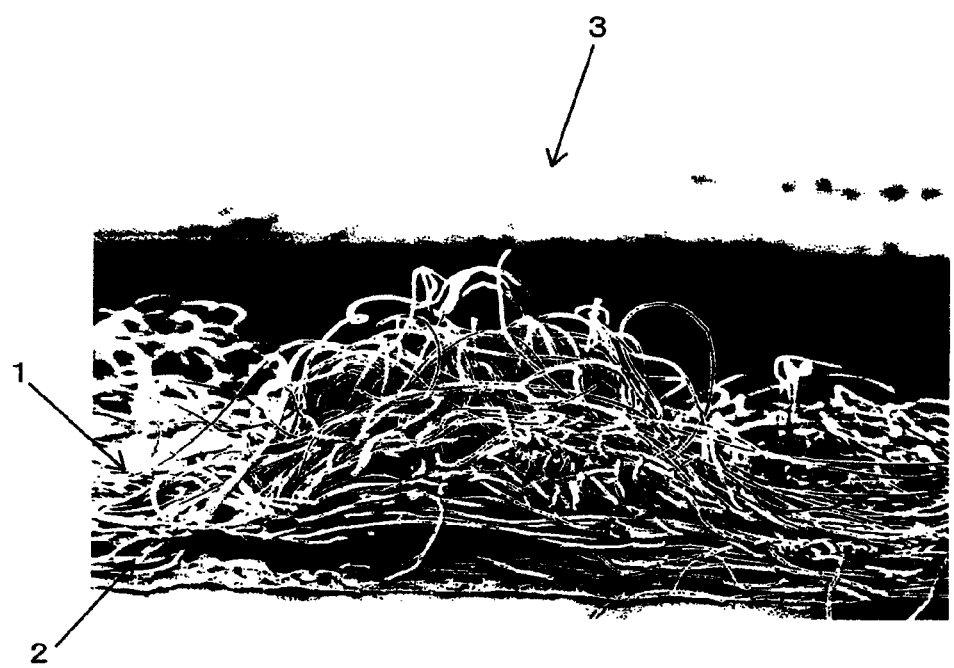
FIG. 3 is a scanning electron micrograph of the cross-section of a projection ($V_{12}$) 4 including no bonded section.

FIG. 3 is a scanning electron micrograph of the cross-section of a projection ($V_{12}$) 4 including no bonded section. In FIG. 3, the top side is the first side 1 and the bottom side is the second side 2. In FIG. 3, the second side 2 does not comprise recesses overlapping projections ($V_{12}$) 4 of the first side 1.

Incidentally, although the second side does not comprise recesses overlapping projections ($V_{12}$) of the first side in the embodiment shown in FIG. 1, in accordance with further embodiment of the invention, the second side may comprise recesses overlapping projections ($V_{12}$) of the first side.

As used herein, the projections ($V_{11}$), each projection ($V_{11}$) including at least one bonded section, the projections ($V_{12}$) including no bonded section and the at least one recess ($C_{11}$), that may be formed on the first side, will also be referred to as "first side irregularities", and the first side containing them will also be referred to as "first side with irregularities".

Also as used herein, the recesses ($C_{21}$), and the optional projections ($V_{21}$) and recesses ($C_n$), that may be formed on the second side, will also be referred to as "second side irregularities", even if projections ($V_{21}$) are not present, and the second side containing them will also be referred to as "second side with irregularities", even if projections ($V_n$) are not present.

Figure 4:
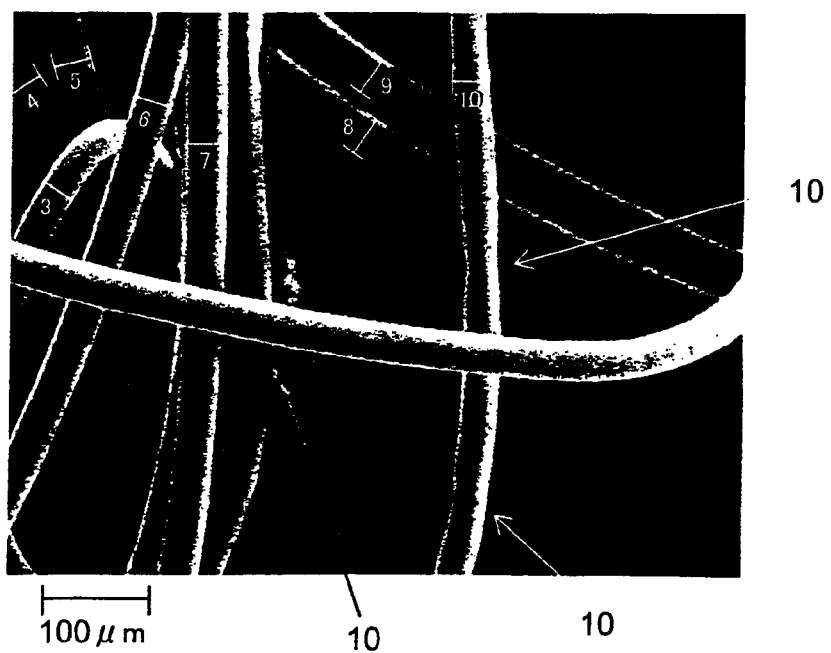
FIG. 4 is a scanning electron micrograph of continuous fibers in the nonwoven fabric shown in FIG. 1.

FIG. 4 is a scanning electron micrograph of continuous fibers in the nonwoven fabric shown in FIG. 1. As shown in FIG. 4, the continuous fibers in the nonwoven fabric of FIG.

1 have a diameter distribution, and the coefficient of variation of the diameters of the continuous fibers is at least 10%. Also, as shown in FIG. 4, the continuous fibers in the nonwoven fabric of FIG. 1 have a plurality of necks 9 with partially narrowed diameters.

As used herein, the term "coefficient of variation" refers to the value obtained by photographing the continuous fibers with an electron microscope or the like, measuring the fiber sizes in the photographed image at 50 arbitrary locations and calculating the value from the standard deviation and arithmetic mean, according to the following formula (1).

$$\text{Coefficient of variation (\%)} = 100 \times \text{standard deviation} / \text{arithmetic mean} \quad \text{Formula (1)}$$

As is clear from the fact that the nonwoven fabric has a coefficient of variation of at least 10% for the diameters of the continuous fibers, sections where the fiber sizes are partially thick and the sections where the fiber sizes are partially thin are mixed among the continuous fibers in the nonwoven fabric. Thus, the nonwoven fabric of the disclosure is soft and easily deformable at the sections with narrow fiber sizes, while being resistant to deformation and collapse, i.e. exhibiting a cushioning property, at the sections with thick fiber sizes.

Also, the first side of the nonwoven fabric of the disclosure comprises a plurality of projections ($V_{11}$), each projection ($V_{11}$) including at least one bonded section, while the second side comprises a plurality of recesses ($C_{21}$), each recess ($C_{21}$) overlapping with at least a part of the projection ($V_{11}$) of the first side. In the nonwoven fabric of the disclosure, therefore, the top sheet of the absorbent article is used in the first side, and when pressure is applied, soft, easily deformable projections and deformation-resistant, anti-collapsible projections are present. As a result, the nonwoven fabric of the disclosure also has a property of being easily deformable and resistant to collapse, due to the coefficient of variation of 10% or greater.

Therefore, the nonwoven fabric of the disclosure having such cushioning properties, is suitable for use as an absorbent article top sheet or the like.

In the nonwoven fabric of the disclosure, the first side preferably comprises the projections ($V_{11}$) at a number density in the range of about 100-10,000/m², the projections ($V_{12}$) at a number density in the range of about 100-10,000/m², and the recess ($C_{11}$) at a number density in the range of about 1-10,000/m², and the second side preferably comprises the recess ($C_{21}$) at a number density in the range of about 100-10,000/m². In addition, in the embodiment in which the second surface further comprises the recess ($C_{22}$), the second surface comprises the recess ($C_{22}$) at a number density in the range of about 1-10,000/m².

Furthermore, the coefficient of variation of the diameters of the continuous fibers is at least 10%, preferably 10-50%, and more preferably 10-20%.

There are no particular restrictions on the material of the continuous fibers, and examples include thermoplastic resins such as polyolefins, including polyethylene, polypropylene, polybutene, polyester, nylon, polystyrene and the like. The continuous fibers may also be composite fibers, such as core-sheath composite fibers, sea-island composite fibers, split mold composite fibers or side-by-side composite fibers.

There are no particular restrictions on the sizes of the continuous fibers, but when used for the top sheet of an absorbent article, they are preferably in the range from about 1 to about 6 dtex. If the sizes of the continuous fibers are less than about 1 dtex the strength of the continuous fibers will be reduced, the thickness of the nonwoven fabric will thus be reduced and the air permeability and liquid permeability of the nonwoven fabric will tend to be lower. If the sizes of the continuous fibers exceed about 6 dtex, the strength of the continuous fibers themselves will increase and the feel will tend to be reduced.

In accordance with an embodiment of the disclosure, the nonwoven fabric may comprise two or more different types of continuous fibers.

The bonded sections may be thermocompression bonded sections, for example.

In the nonwoven fabric, the number of the plurality of projections ($V_{11}$), each projection ($V_{11}$) including at least one bonded section, the number of the plurality of projections ($V_{12}$) including no bonded section and the number of recesses ($C_u$) on the first side, and the number of the plurality of recesses ($C_{21}$), each recess ($C_{21}$) overlapping with at least a part of the projection ($V_{11}$) of the first side on the second side, will vary depending on the performance desired for the nonwoven fabric of the disclosure, but they may be numbers such as to allow formation of a nonwoven fabric, such as a spunbond nonwoven fabric or meltblown nonwoven fabric, comprising continuous fibers and bonded sections formed by bonding multiple fibers including the continuous fibers, when it is subjected to non-homogeneous stretching so that a nonwoven fabric having high-stretch regions and low-stretch regions is formed, the nonwoven fabric having high-stretch regions and low-stretch regions is placed on a support and a fluid is subsequently sprayed onto the nonwoven fabric having high-stretch regions and low-stretch regions, and the numbers can be adjusted by modifying the non-homogeneous stretching step and fluid treatment step.

In an embodiment in which the nonwoven fabric is to be used as a liquid-permeable top sheet in an absorbent article, the nonwoven fabric may be hydrophilic. This will allow contacted hydrophilic excreted fluid (urine, sweat, stool, etc.) to pass through the interior of the absorbent article more easily without remaining on the surface of the nonwoven fabric.

To obtain a nonwoven fabric having hydrophilicity, for example, the nonwoven fabric may be treated with a hydrophilic agent, the nonwoven fabric may be produced from composite fibers incorporating a hydrophilic agent, or the nonwoven fabric may be coated with a surfactant.

In an embodiment of the disclosure, the nonwoven fabric may further comprise staple fibers commonly used in the technical field in addition to the continuous fibers, within a range that allows the effect of the disclosure to be exhibited. Examples of such staple fibers include natural fibers, semi-natural fibers and synthetic fibers. The staple fibers are preferably synthetic fibers. This will increase the flexibility of the nonwoven fabric. In an embodiment of disclosure in which the nonwoven fabric includes staple fibers, the percentage of the staple fibers is preferably no greater than about 30 mass %, more preferably no greater than about 20 mass % and even more preferably no greater than about 10 mass %, with respect to the total amount of fiber.

When the staple fibers are staple fibers composed of synthetic fiber, their addition will tend to be resistant to collapse even when the user applies body pressure, and will tend to have satisfactory air permeability.

The material of staple fibers composed of synthetic fibers may be polyethylene, polypropylene, polyester or the like. From the viewpoint of moldability, the staple fibers preferably have sizes of about 1-6 dtex.

Since the first side of the nonwoven fabric of the disclosure is easily deformable but resistant to collapse, and has excellent cushioning properties, it can be suitably used for the skin contact surface of the top sheet of an absorbent article.

Since the second side of the nonwoven fabric of the disclosure comprises a plurality of recesses ($C_{21}$), each recess ($C_{21}$) overlapping with at least a part of the projection ($V_{11}$), liquids such as sweat, urine and menstrual blood are temporarily stored and do not flow over onto the skin side, and the fabric is therefore suitable for use on the skin contact surface of the top sheet of an absorbent article.

Moreover, in an embodiment in which the second side of the nonwoven fabric of does not contain recesses overlapping with projections ($V_{12}$) of the first side, it is possible to increase the contact area of the second side with contacting substances. In such cases, therefore, using the nonwoven fabric as a top sheet, such that the second side is on the non-skin contact surface side, allows absorbed liquids to rapidly migrate to the absorbent core on the lower layer.

The nonwoven fabric of the disclosure will now be explained in greater detail, with a method of forming a processed nonwoven fabric.

[Method of Forming a Processed Nonwoven Fabric]

The method of forming a processed nonwoven fabric comprises a step of providing a nonwoven fabric comprising continuous fibers and bonded sections formed by bonding multiple fibers including the continuous fibers. The nonwoven fabric used in this step is not particularly restricted so long as it is a nonwoven fabric comprising continuous fibers and bonded sections, and for example, it may be a spunbond nonwoven fabric, meltblown nonwoven fabric or the like comprising the continuous fibers and bonded sections.

Continuous fibers obtained by spunbond or meltblown methods have higher fiber ductility than staple fibers used in carding methods. Thus, the bonded sections are relatively resistant to breakage in the subsequent non-homogeneous stretching step, and readily form high-stretch regions. This provides the advantage of easier formation of the first side with irregularities and/or the second side with irregularities in the subsequent fluid treatment step.

As used herein, the nonwoven fabric provided for this step will sometimes be referred to as "nonwoven fabric before non-homogeneous stretching".

The nonwoven fabric before non-homogeneous stretching may be a commercially available nonwoven fabric, such as a commercially available spunbond nonwoven fabric or meltblown nonwoven fabric.

The nonwoven fabric before non-homogeneous stretching may be hydrophilic, in an embodiment in which the nonwoven fabric formed in the method of forming a nonwoven fabric is to be used as a liquid-permeable top sheet in an absorbent article. This will provide hydrophilicity to the nonwoven fabric formed by the method of forming a nonwoven fabric. The method of imparting hydrophilicity to the nonwoven fabric was described above.

In an embodiment of the disclosure, the nonwoven fabric before non-homogeneous stretching may further comprise staple fibers in addition to the continuous fibers, in a range that allows the effect of the disclosure to be exhibited. In this embodiment, the nonwoven fabric before non-homogeneous stretching may comprise the staple fibers described above, in the percentages mentioned above.

The method of forming a nonwoven fabric of the disclosure comprises a step in which a nonwoven fabric comprising continuous fibers and bonded sections formed by bonding multiple fibers including the continuous fibers, is subjected to non-homogeneous stretching so as to form a nonwoven fabric having high-stretch regions and low-stretch regions (this will hereunder also be referred to as "non-homogeneous stretching step").

In the non-homogeneous stretching step, (i) the continuous fibers are stretched and undergo plastic deformation, especially in the high-stretch regions. The continuous fibers in the nonwoven fabric are randomly orientated, without being oriented in a fixed direction. Thus, for example, when a nonwoven fabric comprising fibers of diameter "a" are stretched "homogeneously" to a factor "b" in a fixed direction, the fibers in the stretched nonwoven fabric are combinations of fibers stretched from between a factor of "1" (unstretched) and a factor of "b", while the diameters have a distribution of a/b-a. In the non-homogeneous stretching step, the nonwoven fabric comprising the continuous fibers stretches not "homogeneously" but "non-homogeneously", and therefore the diameter at any section of the stretched continuous fibers presumably has an even wider distribution.

As a result, the coefficient of variation of the diameters of the continuous fibers in the nonwoven fabric of the disclosure is approximately 10% or greater.

In the non-homogeneous stretching step, a portion of the (ii) bonded sections are often destroyed in addition to (i), especially in the high-stretch regions, so that part of the nonwoven fabric becomes web-like.

Also, when gear stretching as described hereunder is employed in the non-homogeneous stretching step, (iii) the resistance of the fiber surface during stretching is increased at the sections of the continuous fibers with a large number of fibers where the fibers are tangled, especially in the high-stretch regions, often resulting in local stretching of the fibers in the lengthwise direction and creation of neck sections.

The neck sections can serve as origins for fiber bending when pressure is applied, for example, and can therefore impart easy deformability to the nonwoven fabric, but because the neck sections are randomly distributed it is possible to maintain a certain degree of resistance to collapse. From the viewpoint of the neck sections as well, therefore, the nonwoven fabric of the disclosure is suitable as a top sheet for an absorbent article.

As used herein, the term "high-stretch regions" refers to regions within the nonwoven fabric that are stretched so that their degree of extension is greater than the low-stretch regions, and the term "low-stretch regions" refers to regions within the nonwoven fabric that are stretched so that their degree of extension is less than the high-stretch regions, and they include regions without extension, i.e. unstretched regions.

As used herein, the term "non-homogeneous stretching" refers to stretching of the nonwoven fabric so as to form a nonwoven fabric having high-stretch regions and low-stretch regions, or in other words, stretching of the nonwoven fabric so as to form a nonwoven fabric having different degrees of extension depending on the location.

The non-homogeneous stretching step is not particularly restricted so long as it allows formation of a nonwoven fabric with high-stretch regions and low-stretch regions, and it may be carried out by any desired means, such as passing the nonwoven fabric through the gap between a pair of gear rolls each having a rotational axis line perpendicular to the machine direction and rotating while engaging the plurality of teeth arranged around the peripheral surface of each gear roll (this will hereunder also be referred to as "gear stretching").

Figure 5:
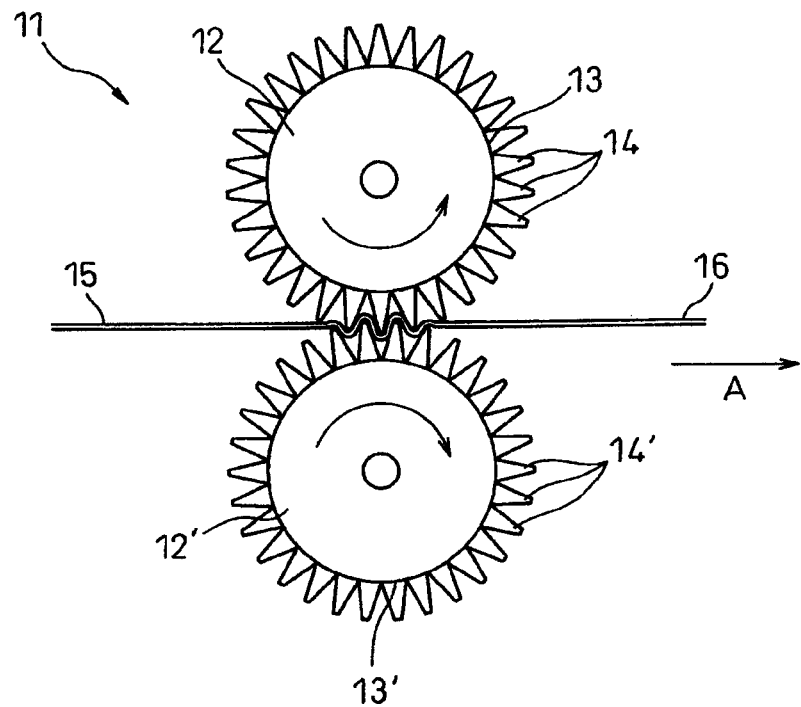
FIG. 5 is a schematic view illustrating a gear stretcher in which a plurality of teeth are arranged around the peripheral surfaces of gear rolls, parallel to the rotational axis lines of the gear rolls.

FIG. 5 is a schematic view illustrating a gear stretcher in which a plurality of teeth are arranged around the peripheral surfaces of gear rolls, parallel to the rotational axis lines of the gear rolls. The gear stretcher 11 shown in FIG. 5 has a pair of gear rolls 12 and 12'. A plurality of teeth 14 and 14' are arranged around the peripheral surfaces 13 and 13' of each of the gear rolls 12 and 12'. In the gear stretcher 11 shown in FIG. 4, the rotational axis lines of the gear rolls 12 and 12' are both perpendicular to the machine direction A. The plurality of teeth 14 and 14' are arranged parallel to the rotational axis lines of the respective peripheral surfaces 13 and 13'.

In the gear stretcher 11 shown in FIG. 5, the nonwoven fabric 15 comprising continuous fibers and bonded sections formed by bonding multiple fibers including the continuous fibers is passed through the roll gap between a pair of gear rolls 12 and 12', and as it passes through the gear rolls 12 and 12', the nonwoven fabric 15 comprising continuous fibers and bonded sections formed by bonding multiple fibers including the continuous fibers is stretched by the plurality of teeth 14 and 14' of the engaging gear rolls 12 and 12', according to the three-point bending principle, thus forming a nonwoven fabric having high-stretch regions and low-stretch regions 16. The nonwoven fabric 16 having high-stretch regions and low-stretch regions has alternating high-stretch regions and low-stretch regions in the machine direction A, which are parallel to the direction that is perpendicular to the machine direction A (hereunder, the direction perpendicular to the machine direction will be referred to simply as the "cross direction").

In the nonwoven fabric 15 comprising continuous fibers and bonded sections formed by bonding of multiple fibers including the continuous fibers, the fabric of the nonwoven fabric is anchored in the regions that are in contact with the tips of the plurality of teeth 14 and 14', and therefore undergoes little or no stretching, forming the low-stretch regions. On the other hand, large stretching occurs in the regions that are not in contact with the tips of the plurality of teeth 14 and 14', forming the high-stretch regions.

Also, as mentioned above, particularly in the high-stretch regions, (i) the continuous fibers are stretched and undergo plastic deformation, so that the coefficient of variation of the diameters of the continuous fibers is approximately 10% or greater, (ii) some of the bonded sections are destroyed, often causing webbing of part of the nonwoven fabric, and (iii) at the sections of numerous continuous fibers where the fibers are tangled, the resistance of the fiber surface during stretching is increased, causing local stretching of the fibers in the lengthwise direction and often forming neck sections.

Figure 6:
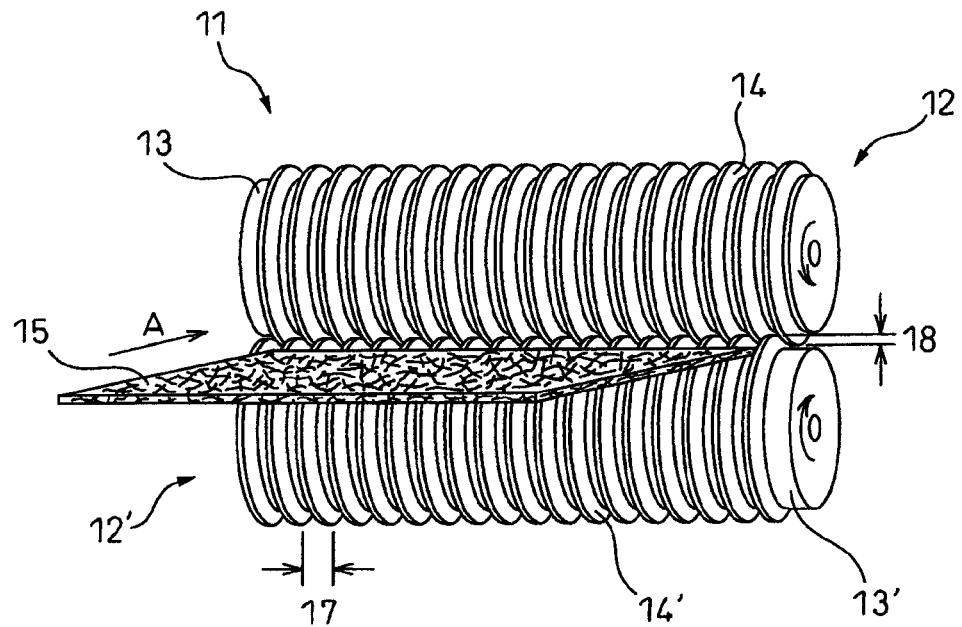
FIG. 6 is a schematic view illustrating a gear stretcher in which a plurality of teeth are arranged around the peripheral surfaces of gear rolls, perpendicular to the rotational axis lines of the gear rolls.

Gear stretching can also be accomplished using a gear stretcher as shown in FIG. 6.

FIG. 6 is a schematic view illustrating a gear stretcher in which a plurality of teeth are arranged around the peripheral surfaces of gear rolls, perpendicular to the rotational axis lines of the gear rolls. FIG. 6 is a perspective view of the gear stretcher 11, and it shows the state of the nonwoven fabric 15 comprising continuous fibers and bonded sections formed by bonding multiple fibers including the continuous fibers, just prior to gear stretching. The nonwoven fabric 15 comprising continuous fibers and bonded sections formed by bonding multiple fibers including the continuous fibers undergoes gear stretching by proceeding from foreground to background.

The gear stretcher 11 shown in FIG. 6 has a pair of gear rolls 12 and 12'. A plurality of teeth 14 and 14' are arranged around the peripheral surfaces 13 and 13' of the gear rolls 12 and 12'. In the gear stretcher 11 shown in FIG. 6, the plurality of teeth 14 and 14' are arranged on the respective peripheral surfaces 13 and 13' in a manner perpendicular to the rotational axis lines of the gear rolls 12 and 12'. When the plurality of teeth 14 and 14' are arranged in this manner, it is possible to form a nonwoven fabric having parallel high-stretch regions and low-stretch regions, parallel to the machine direction, alternating in the cross direction.

The gear stretcher may also have a plurality of teeth arranged around the peripheral surfaces of gear rolls, and slanted with respect to the rotational axis lines of the gear rolls.

Figure 7:
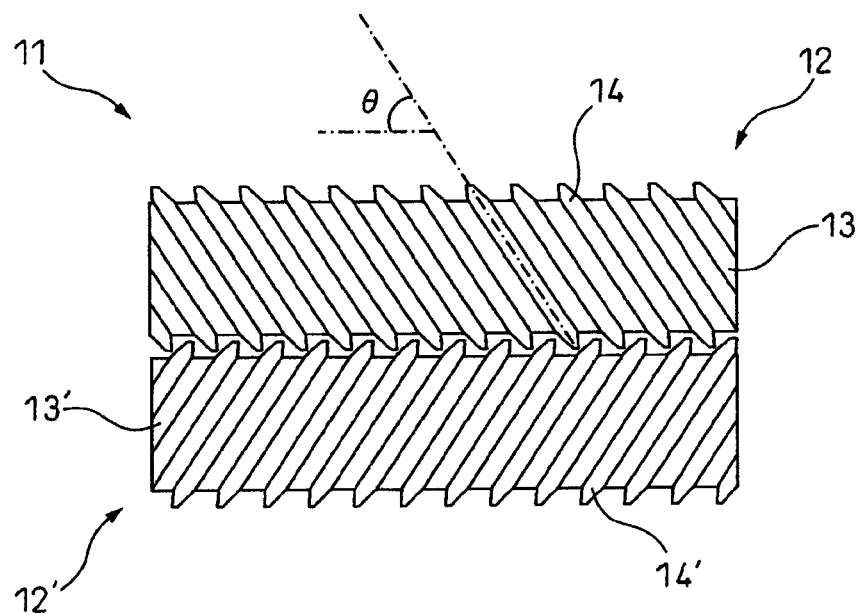
FIG. 7 is a schematic view illustrating a gear stretcher in which a plurality of teeth are arranged around the peripheral surfaces of gear rolls, slanted with respect to the rotational axis lines of the gear rolls.

FIG. 7 is a schematic view illustrating a gear stretcher in which a plurality of teeth are arranged around the peripheral surfaces of gear rolls, slanted with respect to the rotational axis lines of the gear rolls. The gear stretcher 11 shown in FIG. 7 has a pair of gear rolls 12 and 12'. A plurality of teeth 14 and 14' are arranged around the peripheral surfaces 13 and 13' of the gear rolls 12 and 12'. In the gear stretcher 11 shown in FIG. 7, the rotational axis lines of the gear rolls 12 and 12' are both perpendicular to the machine direction A. The plurality of teeth 14 and 14' are arranged around the peripheral surfaces 13 and 13' at a fixed angle of θ with respect to the rotational axis line.

The gear stretcher may be appropriately selected depending on the desired performance for the nonwoven fabric to be formed by the method of forming a nonwoven fabric of the dislcosure.

For example, when high extensibility is required in both the machine direction and its cross direction, the nonwoven fabric before non-homogeneous stretching may be stretched using the gear stretcher shown in FIG. 5, and then the gear stretcher shown in FIG. 6 may be used for further stretching.

Also, the nonwoven fabric before non-homogeneous stretching may be stretched using the gear stretcher shown in FIG. 6, after which the gear stretcher shown in FIG. 5 may be used for further stretching.

In the gear stretchers shown in FIGS. 5 to 7, the gear pitch is preferably about 1-10 mm and more preferably about 2-6 mm. If the gear pitch is less than about 1 mm it may be necessary to reduce the thickness of the gear blades and portions of the nonwoven fabric may be severed, while if the gear pitch is greater than about 10 mm, the stretch ratio may be reduced and insufficiencies may result, including plastic deformation of the continuous fibers, webbing of portions of the nonwoven fabric and formation of neck sections.

The gear pitch is the interval between adjacent teeth, and it is denoted by numeral 17 in FIG. 6.

In this gear stretcher, the gear tooth cutting depth is preferably about 0.5 mm or greater. If the gear tooth cutting depth is less than about 0.5 mm, insufficiencies may result, including a low stretch ratio, plastic deformation of the continuous fibers, webbing of portions of the nonwoven fabric and formation of neck sections.

The gear tooth cutting depth is the depth at the section where the top gear roll tooth and bottom gear roll tooth overlap, and it is denoted by numeral 18 in FIG. 6.

In a nonwoven fabric having high-stretch regions and low-stretch regions, the stretch ratio is preferably about 30-400% and more preferably about 50-200%. If the stretch ratio is less than about 30%, insufficiencies may result such as a low stretch ratio, plastic deformation of the continuous fibers, webbing of portions of the nonwoven fabric and formation of neck sections, while if the stretch ratio is greater than about 400%, the strength of the nonwoven fabric having high-stretch regions and low-stretch regions may be weak, the extended fibers may tend to shed off, and transport may be impeded.

As used herein, the term "stretch ratio" refers to the value calculated by the following formula:

$$\text{Stretch ratio (\%)} = 100 \times \left[ \frac{\sqrt{P^2 + 4D^2}}{P} - 1 \right] \quad \text{[Formula 1]}$$

where P is the gear pitch and D is the gear tooth cutting depth.

The reel-off speed of the nonwoven fabric before non-homogeneous stretching will vary depending on the desired stretch ratio, but it may be about 10 m/min or greater, for example.

The method of forming a nonwoven fabric according to the disclosure comprises a step of placing the nonwoven fabric having high-stretch regions and low-stretch regions on a support, and spraying a fluid onto the nonwoven fabric having high-stretch regions and low-stretch (this will hereunder be referred to as "fluid treatment step").

Figure 8:
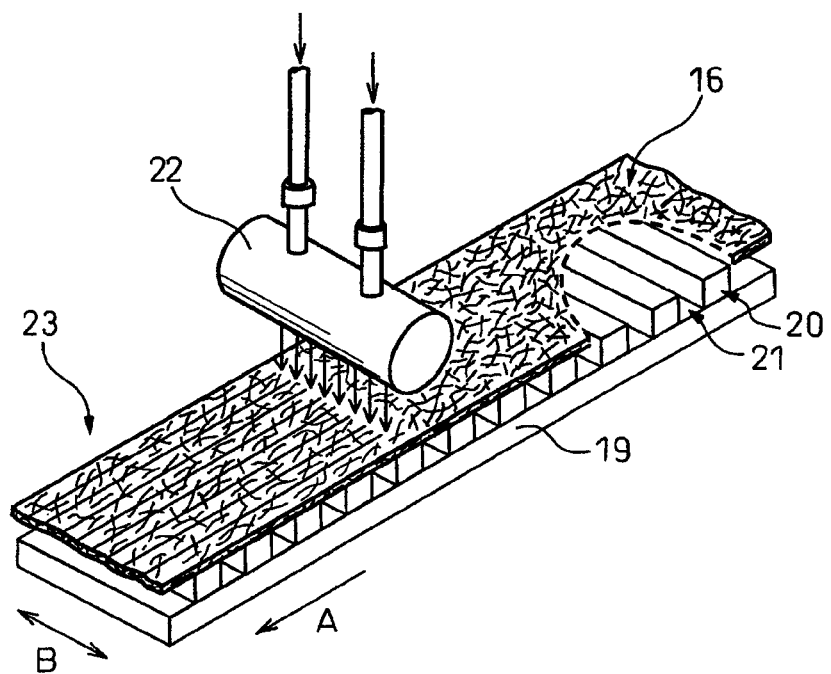
FIG. 8 is a diagram showing an example of a fluid treatment step.

FIG. 8 is a diagram showing an example of a fluid treatment step. The support 19 shown in FIG. 8 has protrusions 20 and depressions 21 running parallel in the cross direction B, and the protrusions 20 and depressions 21 are arranged in an alternating fashion in the machine direction A. In FIG. 8, the protrusions 20 and depressions 21 have cubic shapes.

A fluid nozzle 22 is also shown in FIG. 8, and below the fluid nozzle 22 there is provided a suction section (not shown) that receives fluid, sandwiching the support 19.

A fluid is blasted from the fluid nozzle 22 onto a nonwoven fabric having high-stretch regions and low-stretch regions 16 that has been placed on a support 19 and has been carried in, thus forming a nonwoven fabric 23 having a specific form and specific coefficient of variation. The blasted fluid is discharged from the suction section (not shown).

Figure 9:
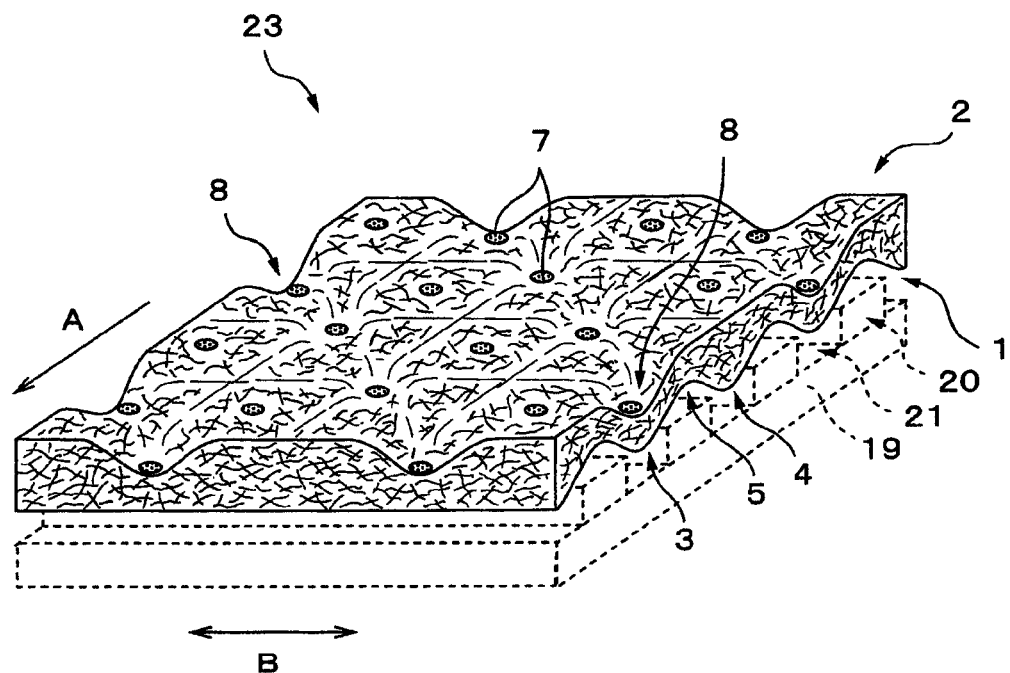
FIG. 9 is a diagram illustrating an example of a nonwoven fabric formed using the support 19 shown in FIG. 8.

FIG. 9 shows an example of a nonwoven fabric formed using a support 19 as shown in FIG. 8. In the nonwoven fabric 23 having a specific form and specific coefficient of variation shown in FIG. 9, the upper side is the second side 2 and the lower side is the first side 1. Also the support 19 is indicated by a dotted line in FIG. 9, for easier understanding.

In the fluid treatment step, the side on which the fluid impacts (hereunder referred to as "fluid-impacting side") corresponds to the second side, and the side opposite the fluid-impacting side (hereunder referred to as "non-fluid-impacting side") corresponds to the first side.

The sprayed fluid from the fluid nozzle 22 flows through the nonwoven fabric having high-stretch regions and low-stretch regions 16, and upon impacting the support 19 and protrusion 20, it flows into the depressions 21. As a result, the extended continuous fibers that have a high degree of freedom move with the fluid flow toward the depressions 21, such that the amount of continuous fiber per unit area is reduced at the locations where the fluid and the protrusions 20 cross, forming recesses ($C_{11}$) 5 in the nonwoven fabric having high-stretch regions and low-stretch regions 16, while the amount of continuous fiber per unit area is increased at the locations where the fluid and the depressions 21 cross, forming in the nonwoven fabric having high-stretch regions and low-stretch regions 16, two types of projections: specifically projections ($V_{11}$) 3, each projection ($V_{11}$) including at least one bonded section and projections ($V_{12}$) 4 including no bonded section.

In the projections ($V_{11}$) 3, each projection ($V_{11}$) including at least one bonded section, when the extended continuous fibers migrate along with the fluid flow toward the depressions 21, the fluid causes the bonded sections 7 to migrate toward the depressions 21, together with the continuous fibers surrounding the bonded sections 7, and especially the continuous fibers surrounding the bonded sections 7 on the second side. As a result, the second side 2 comprises a plurality of recesses ($C_{21}$) 8, each recess ($C_{21}$) overlapping with at least a part of the projection ($V_{11}$) 3 of the first side 1. The reason for "at least a part" is so that when the bonded section is at the perimeters of the projection, the recess on the second side either will not form, or even if recess does form on the second side, it will not overlap with projection ($V_{11}$) 3.

The bonded sections of a spunbond nonwoven fabric, meltblown nonwoven fabric or the like are usually thinner than the sections other than the bonded sections, but the thicknesses of the bonded sections are not reflected in FIG. 9. It was presumed that their illustration would interfere with understanding of the irregularities formed in the fluid treatment step.

In the projections ($V_{11}$), each projection ($V_{11}$) including at least one bonded section and the projections ($V_{12}$) including no bonded section, the extended continuous fibers tend to rise in the thickness direction of the nonwoven fabric, and therefore the compression resistance and liquid permeability of the nonwoven fabric of the disclosure is improved. In addition, the presence of the irregularities on the first side results in excellent air permeability of the nonwoven fabric of the disclosure, particularly excellent air permeability in the planar direction, and superior feel on the skin due to reduced contact area.

In the fluid treatment step, as the sprayed fluid impacts with the fluid-impacting side and then bounces off, it is divided in planar directions, such as the cross direction, depending on the basis weight of the nonwoven fabric having high-stretch regions and low-stretch regions, the stretch ratio in the non-homogeneous stretching step, and the type and amount of sprayed fluid, so that in some cases the second side will further comprise a plurality of projections ($V_{21}$) and a plurality of recesses ($C_{22}$). The recesses ($C_{22}$) on the second side differ from the recesses ($C_{21}$) in their route of formation, and as a rule the recesses ($C_{22}$) do not overlap with the projections ($V_{11}$) of the first side.

When the second side also comprises a plurality of projections ($V_{21}$) and a plurality of recesses ($C_{22}$) in addition to the recesses ($C_{21}$), the second side will often have a complex surface form resulting from their combination.

In some cases, at least one recess ($C_{11}$) on the first side and at least one recess ($C_{22}$) on the second side becomes connected, forming at least one open hole. The recesses ($C_{22}$) on the second side are formed as the sprayed fluid impacts and bounces off, but when the sprayed fluid has high energy, the fibers become even more divided and may form larger recesses ($C_{22}$) on the second side directly under the sprayed fluid. Consequently, at least one recess ($C_{11}$) may be present on the first side opposite the larger recesses ($C_{22}$) on the second side, while formation of the nonwoven fabric before non-homogeneous stretching and the local degree of stretching during non-homogeneous stretching are sometimes accompanied by formation of at least one open hole where at least one recess ($C_{11}$) on the first side and at least one recess ($C_{22}$) on the second side is connected.

In the embodiment in which the nonwoven fabric has one or more open holes, the nonwoven fabric has the open holes at a number density in the range of about 100-10,000/$m^2$. As used herein, the open hole means the area in which the distance between two fibers is 0.3 mm or more.

When the nonwoven fabric has a first side with irregularities and/or a second side with irregularities, the contact area with the skin is reduced, which can reduce the feeling of stickiness caused by mustiness resulting from a large contact area, as well as the feeling of irritation caused by rubbing, and it is therefore suitable for purposes such as absorbent articles.

FIG. 8 shows a support 19 having protrusions 20 and depressions 21 arranged parallel to the cross direction and alternating in the machine direction, but there are no particular restrictions on the shape of the support for the method of forming a nonwoven fabric of the invention. In embodiments of the disclosure, the support include: (i) a support having protrusions and depressions that are all parallel to the machine direction and alternatingly disposed in the cross direction, (ii) a support having protrusions and depressions that are slanted with respect to the machine direction and alternatingly disposed in the direction perpendicular to the slanted direction, or (iii) a support having protrusions and/or depressions having predetermined shapes (for example, cubic, cylindrical or hemispherical) may be disposed in a predetermined arrangement (for example, a heart-shaped or star-shaped arrangement).

The protrusions preferably have lower fluid permeability than the fluid permeability of the depressions. This is because with low fluid permeability at the protrusions, the fluid impacting the protrusions will flow toward the depressions, thus allowing formation of greater projections in the nonwoven fabric formed by the method described above.

The material of the protrusions may be metal, plastic or other suitably strong material.

The shapes and materials of the protrusions and depressions are not particularly restricted, and the support may be formed by situating cubic or tubular-shaped metal in a predetermined arrangement, maintaining a fixed spacing, for example, on a metal or plastic conveyor net, paper-making net or punching plate that is commonly used as a fluid-permeable support.

Examples of supports having protrusions and/or depressions with predetermined shapes (for example, cubic, cylindrical or hemispherical) arranged in a predetermined form (for example, heart-shaped or star-shaped) include supports having hemispherical metal situated in a predetermined arrangement (such as a heart-shaped arrangement) on a punching plate. When such a support is used, it is possible to form a nonwoven fabric having recesses in a predetermined pattern (for example, heart-shaped).

Also, by using a support with protrusions and depressions, in which hemispherical dent shapes are arranged in a predetermined pattern (such as a heart-shaped pattern) on a punching plate, it is possible to form a nonwoven fabric having projections in a predetermined pattern (such as a heart-shaped pattern).

The punching plate itself may also be used as the support. Examples of punching plates that may be used as supports include round hole-type punching plates, such as round hole 60° zigzag types, round hole square zigzag types and round hole serial types, ratchet types, round cross types, cloud types, and cloud zigzag types. When a punching plate is used as the support, the plate sections serve as the protrusions and the open sections serve as the depressions.

By selecting the shape of the support for the method of forming a nonwoven fabric, it is possible to impart a desired pattern, desired air permeability and desired flexibility to the nonwoven fabric before non-homogeneous stretching, and thus accomplish easy and inexpensive modification of commercially available nonwoven fabrics according to desired purposes.

When the fluid treatment step is to be carried out on a roll, a roll-like support may be used, having the outer periphery constructed of a fluid-permeable material such as a mesh and having protrusions and depressions situated with predetermined shapes and a predetermined arrangement, on the peripheral surface. The predetermined shapes and arrangement may be the shapes and arrangement described above.

In a support having protrusions and depressions, their widths will differ depending on the properties required for the nonwoven fabric having a specific form and specific coefficient of variation, but as an example, the support shown in FIG. 8 preferably has protrusion widths in the range of about 0.5 to about 10 mm, and depression widths in the range of about 1 to about 10 mm.

The fluid used in the fluid treatment step may be air, such as heated air or water vapor, such as saturated steam or superheated steam, or water such as hot water. In order to render subsequent drying either unnecessary or only minimally necessary, the fluid is preferably heated air, saturated steam or superheated steam.

The fluid may be blasted from an anchored fluid nozzle onto the nonwoven fabric having high-stretch regions and low-stretch regions, or it may be blasted from a fluid nozzle that is reciprocating in the cross direction. The fluid may also be continuously or intermittently blasted from a fluid nozzle onto the nonwoven fabric having high-stretch regions and low-stretch regions. These may also be used in combinations.

The fluid may be appropriately selected depending on the form of the nonwoven fabric having high-stretch regions and low-stretch regions. For example, for treatment of a nonwoven fabric with a low gear pitch and a large stretch ratio, a nonwoven fabric having a specific form and specific coefficient of variation may be formed with relatively low energy, and therefore air or water vapor is preferably selected as the fluid. Since the bonded sections between continuous fibers are increased in number when using a nonwoven fabric with a large gear pitch and many low-stretch regions, a relatively high energy is necessary to form a nonwoven fabric with a specific form and specific coefficient of variation, and therefore water or water vapor is preferably selected as the fluid, with water vapor being more preferred. This is because moisture does not easily remain in the sections with a large continuous fiber content and the bonded sections between the sections with a high continuous fiber content are not usually destroyed, so that the extended continuous fibers in the sections that are to undergo movement can be easily moved.

The fluid treatment step can be carried out by a known method using an apparatus known in the technical field.

When the fluid is heated air, the pressure and temperature thereof are preferably 0.01-0.1 MPa and 100-300° C., respectively, when the fluid is saturated steam, the pressure and temperature thereof are preferably 0.1-0.8 MPa and 100-170° C., respectively, and when the fluid is superheated steam, the pressure and temperature thereof are preferably 0.01-0.1 MPa and 100-300° C., respectively.

A nonwoven fabric of the disclosure or a nonwoven fabric formed by the method of the disclosure is useful for absorbent articles such as sanitary products and disposable diapers, cleaning products such as wipers, and medical goods such as masks.

A nonwoven fabric formed by the method described above can be used as a liquid-permeable top sheet for an absorbent article, for example. By using a nonwoven fabric that easily deforms but is resistant to collapse, and exhibits excellent air permeability in the planar direction, it is possible to produce similarly superior absorbent articles.

Such an absorbent article may comprise a nonwoven fabric as the liquid-permeable top sheet, a liquid-impermeable back sheet, and an absorbent core between the liquid-permeable top sheet and the liquid-impermeable back sheet.

EXAMPLES

The disclosure will now be explained in greater detail using examples and comparative examples, with the understanding that the disclosure is in no way limited by the examples.

The evaluated properties and measuring conditions in the examples and comparative examples were as follows.

[Basis Weight]

The basis weight was measured according to JIS L 1906, 5.2.

[Bulk]

The bulk was measured using a THICKNESS GAUGE UF-60 by Daiei Kagaku Seiki Mfg. Co., Ltd.

[Compression Property]

The compression property was evaluated using a KES-FB3 automated compression tester by Kato Tech Corp.

The measuring conditions were as follows.
SENS: 2
Speed: 0.02 mm/sec
Stroke: 5 mm/10 V
Compression area: 2 cm$^2$
Uptake interval: 0.1 second
Load limit: 50 g/cm$^2$
Repeat frequency: 1

The compression property was evaluated from WC as the compressional energy per 1 cm$^2$ of nonwoven fabric, $T_0$ as the thickness of the sample at a pressure of 0.5 gf/cm$^2$, and $T_m$ as the thickness of the sample at a pressure of 50 gf/cm$^2$. A larger value for WC indicates easier compression.

[Air Permeability]

The air permeability was measured using a KES-F8-AP1 air permeability tester by Kato Tech Corp., with calculation in units of m$^3$/m$^2$/min.

The air permeability in the thickness direction of the nonwoven fabric was measured by setting the nonwoven fabric, cut to a size of 100 mm×100 mm, in the air permeability tester.

The air permeability in the planar direction of the nonwoven fabric was measured with the nonwoven fabric cut to a size of 100 mm×100 mm and set in the air permeability tester, a 100 mm×100 mm acrylic board set thereover and application of a pressure of 3.5 mN/cm$^2$.

[Liquid Permeability]

The liquid permeability was evaluated using a LISTER strikethrough tester by Lenzing AG. The evaluation procedure was as follows.

(1) The sample cut to a size of 100×100 mm was placed on 5 sheets of filter paper (Advantec Filter Paper Grade 2) cut to sizes of 100×100 mm, and an electrical liquid permeation plate was placed thereover.

(2) The filter paper, sample and electrical liquid permeation plate were set on the strikethrough tester.

(3) A 5 mL portion of physiological saline was poured into the strikethrough tester.

(4) The physiological saline (room temperature) was allowed to drop from the strikethrough tester through an open hole in the electrical liquid permeation plate.

(5) The electrification time of the electrical liquid permeation plate was recorded.

(6) The measurement was repeated twice and the average value for the total of 3 times was recorded as the liquid permeation time.

When no sample was set, i.e. with only 5 filter paper sheets, the liquid permeation time was 69 seconds.

Example 1

Preparation of Nonwoven Fabric

A spunbond nonwoven fabric 1 was prepared. The spunbond nonwoven fabric 1 was a commercially available product comprising continuous fibers made of polypropylene. The spunbond nonwoven fabric 1 had been subjected to square zigzag embossing with round holes, with an embossing diameter of about 0.5 mm, and an MD pitch and CD pitch of about 2 mm and about 2 mm, respectively.

The property values of the spunbond nonwoven fabric 1 are shown in Table 1.

—Gear Stretching—

The spunbond nonwoven fabric 1 was subjected to gear stretching using a gear stretcher such as shown in FIG. 6 (gear pitch: 2.5 mm, gear tip width: 0.2 mm, gear tooth cutting depth: 2.0 mm), to form a nonwoven fabric having high-stretch regions and low-stretch regions. The throughput was 30 m/min. The stretch ratio of the nonwoven fabric having high-stretch regions and low-stretch regions was 89%.

The property values of the nonwoven fabric having high-stretch regions and low-stretch regions are shown in Table 1.

—Steam Treatment—

The nonwoven fabric having high-stretch regions and low-stretch regions was placed on a support consisting of a 60° zigzag punching plate with round holes (φ: 3.0 mm, MD pitch: 6.93 mm, CD pitch: 4.0 mm, thickness: 1.0 mm). Next, the nonwoven fabric having high-stretch regions and low-stretch regions was passed through a steam treatment system comprising a plurality of nozzles (φ: 0.5 mm) at 1.0 mm spacings (spray pressure: 0.5 Mpa, water vapor temperature: approximately 149° C.), at a speed of 30 m/min while maintaining a distance of 2.0 mm between the nozzles and support, to obtain a nonwoven fabric 1.

The property values of the nonwoven fabric 1 are shown in Table 1.

Example 2

A nonwoven fabric 2 was obtained in the same manner as Example 1, except that the gear tooth cutting depth was 3.0 mm and the stretch ratio was changed to 160%. The property values of the nonwoven fabric 2 are shown in Table 1.

Comparative Example 1

A nonwoven fabric 3 was obtained in the same manner as Example 1, except that the spunbond nonwoven fabric 1 was subjected directly to steam treatment without passing through a gear stretching step. The property values of the nonwoven fabric 3 are shown in Table 1.

TABLE 1

| | | Example No. | | |
|---|---|---|---|---|
| | | Example 1 | Example 2 | Comp. Ex. 1 |
| | | Nonwoven fabric No. | | |
| | | Nonwoven fabric 1 | Nonwoven fabric 2 | Nonwoven fabric 3 |
| Initial properties | | | | |
| Fibers | Diameter (μm) | | | 14.5 |
| | CV(%) | | | 8.1 |
| Basis weight | g/m$^2$ | | | 17.2 |
| Bulk | mm | | | 0.15 |

TABLE 1-continued

| | | Example No. | | |
|---|---|---|---|---|
| | | Example 1 | Example 2 | Comp. Ex. 1 |
| | | Nonwoven fabric No. | | |
| | | Nonwoven fabric 1 | Nonwoven fabric 2 | Nonwoven fabric 3 |
| Compression properties | WC(N * m/m²) | | 0.07 | |
| | T₀(mm) | | 0.16 | |
| | Tₘ(mm) | | 0.08 | |
| Air permeability (thickness direction) | m³/m²/min | | 230 | |
| Air permeability (planar direction) | m³/m²/min | | 0.3 | |
| Liquid permeability | Liquid permeation time (sec) | | 45 | |
| Properties after gear stretching | | | | |
| Basis weight | g/m² | 15.6 | 14.2 | |
| Bulk | mm | 0.38 | 0.38 | |
| Compression properties | WC(N * m/m²) | 0.58 | 0.46 | |
| | T₀(mm) | 0.81 | 0.64 | |
| | Tₘ(mm) | 0.19 | 0.12 | |
| Air permeability (thickness direction) | m³/m²/min | 510 | 730 | |
| Air permeability (planar direction) | m³/m²/min | 5 | 5 | |
| Properties after steam treatment | | | | |
| Fibers | Diameter (μm) | 13.2 | 12.3 | 14.5 |
| | CV(%) | 14.1 | 13.5 | 8.1 |
| Basis weight | g/m² | 16.1 | 15.2 | 16.1 |
| Bulk | mm | 0.47 | 0.50 | 0.29 |
| Compression properties | WC(N * m/m²) | 0.65 | 0.65 | 0.21 |
| | T₀(mm) | 1.01 | 1.08 | 0.42 |
| | Tₘ(mm) | 0.15 | 0.15 | 0.14 |
| Air permeability (thickness direction) | m³/m²/min | 760 | 1470 | 410 |
| Air permeability (planar direction) | m³/m²/min | 16 | 13 | 1 |
| Liquid permeability | Liquid permeation time (sec) | — | — | — |

Example 3

A spunbond nonwoven fabric 2 was prepared. The spunbond nonwoven fabric 2 was composed of core-sheath composite fibers having a core made of polypropylene and a sheath made of ethylene/propylene copolymer. The spunbond nonwoven fabric 2 had been subjected to square zigzag embossing, with embossing in rhomboid shapes of approximately 0.6 mm×approximately 0.6 mm, with an MD pitch and CD pitch of about 2 mm and about 2 mm, respectively. The property values of the spunbond nonwoven fabric 2 are shown in Table 2.

A nonwoven fabric 4 was obtained in the same manner as Example 1, except that the spunbond nonwoven fabric 1 was changed to the spunbond nonwoven fabric 2, the spray pressure of the water vapor was changed to 0.4 Mpa, and the water vapor temperature was changed to approximately 141° C. The property values of the nonwoven fabric 4 are shown in Table 2.

Example 4

A nonwoven fabric 5 was obtained in the same manner as Example 3, except that the gear tooth cutting depth was 3.0 mm and the stretch ratio was changed to 160%. The property values of the nonwoven fabric 5 are shown in Table 2.

Comparative Example 2

A nonwoven fabric 6 was obtained in the same manner as Example 3, except that the spunbond nonwoven fabric 2 was subjected directly to steam treatment without gear stretching. The property values of the nonwoven fabric 6 are shown in Table 2.

TABLE 2

| | | Example No. | | |
|---|---|---|---|---|
| | | Example 3 | Example 4 | Comp. Ex. 2 |
| | | Nonwoven fabric No. | | |
| | | Nonwoven fabric 4 | Nonwoven fabric 5 | Nonwoven fabric 6 |
| Initial properties | | | | |
| Fibers | Diameter (μm) | | 19.0 | |
| | CV(%) | | 6.4 | |
| Basis weight | g/m² | | 18.8 | |
| Bulk | mm | | 0.29 | |
| Compression properties | WC(N * m/m²) | | 0.11 | |
| | T₀(mm) | | 0.23 | |
| | Tₘ(mm) | | 0.12 | |
| Air permeability (thickness direction) | m³/m²/min | | 330 | |
| Air permeability (planar direction) | m³/m²/min | | 0.4 | |
| Liquid permeability | Liquid permeation time (sec) | | 32 | |
| Properties after gear stretching | | | | |
| Basis weight | g/m² | 17.1 | 16.6 | |
| Bulk | mm | 0.48 | 0.52 | |
| Compression properties | WC(N * m/m²) | 0.53 | 0.64 | |
| | T₀(mm) | 0.82 | 0.95 | |
| | Tₘ(mm) | 0.12 | 0.16 | |
| Air permeability (thickness direction) | m³/m²/min | 1010 | 1560 | |
| Air permeability (planar direction) | m³/m²/min | 16 | 18 | |
| Properties after steam treatment | | | | |
| Fibers | Diameter (μm) | 18.6 | 17.5 | 19.0 |
| | CV(%) | 12.6 | 10.7 | 6.4 |
| Basis weight | g/m² | 19.3 | 17.6 | 19.5 |
| Bulk | mm | 0.56 | 0.62 | 0.44 |
| Compression properties | WC(N * m/m²) | 0.82 | 0.86 | 0.46 |
| | T₀(mm) | 1.16 | 1.23 | 0.78 |
| | Tₘ(mm) | 0.24 | 0.22 | 0.16 |
| Air permeability (thickness direction) | m³/m²/min | 880 | 2140 | 780 |
| Air permeability (planar direction) | m³/m²/min | 24 | 26 | 13 |
| Liquid permeability | Liquid permeation time (sec) | — | — | — |

Example 5

Figure 10:
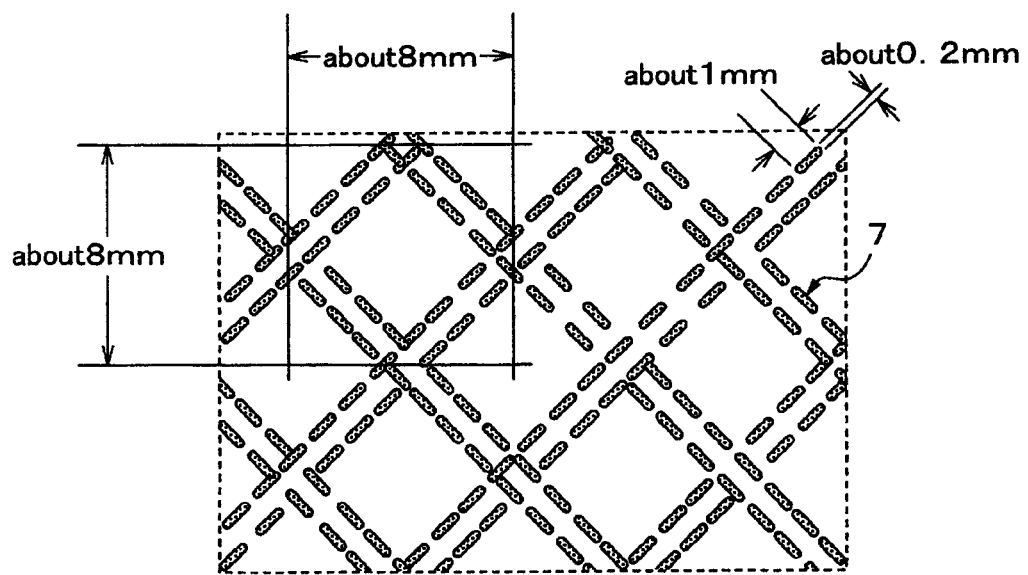
FIG. 10 is a diagram illustrating embossing of the spunbond nonwoven fabrics used in Example 5 and Comparative Example 3.

A spunbond nonwoven fabric 3 was prepared. The spunbond nonwoven fabric 3 was composed of core-sheath composite fibers having a core made of polypropylene and a sheath made of ethylene/propylene copolymer. Bonded sections 7 were situated as embossing on the spunbond nonwoven fabric 3, as shown in FIG. 10. The property values of the spunbond nonwoven fabric 3 are shown in Table 3.

A nonwoven fabric 7 was obtained in the same manner as Example 3, except that the spunbond nonwoven fabric 2 was changed to the spunbond nonwoven fabric 3, the gear tooth cutting depth was changed to 2.5 mm and the stretch ratio was changed to 124%. The property values of the nonwoven fabric 7 are shown in Table 3.

Comparative Example 3

A nonwoven fabric 8 was obtained in the same manner as Example 5, except that the spunbond nonwoven fabric 3 was subjected directly to steam treatment without passing through a gear stretching step. The property values of the nonwoven fabric 8 are shown in Table 3.

TABLE 3

| | | Example No. | |
|---|---|---|---|
| | | Example 5 | Comp. Ex. 3 |
| | | Nonwoven fabric No. | |
| | | Nonwoven fabric 7 | Nonwoven fabric 8 |
| Initial properties | | | |
| Fibers | Diameter (μm) | | 20.0 |
| | CV(%) | | 5.5 |
| Basis weight | g/m$^2$ | | 28.4 |
| Bulk | mm | | 0.31 |
| Compression properties | WC(N * m/m$^2$) | | 0.21 |
| | $T_0$(mm) | | 0.43 |
| | $T_m$(mm) | | 0.18 |
| Air permeability (thickness direction) | m$^3$/m$^2$/min | | 300 |
| Air permeability (planar direction) | m$^3$/m$^2$/min | | 1.0 |
| Liquid permeability | Liquid permeation time (sec) | | 25 |
| Properties after gear stretching | | | |
| Basis weight | g/m$^2$ | 24.9 | |
| Bulk | mm | 0.92 | |
| Compression properties | WC(N * m/m$^2$) | 0.80 | |
| | $T_0$(mm) | 1.19 | |
| | $T_m$(mm) | 0.16 | |
| Air permeability (thickness direction) | m$^3$/m$^2$/min | 820 | |
| Air permeability (planar direction) | m$^3$/m$^2$/min | 43 | |
| Properties after steam treatment | | | |
| Fibers | Diameter (μm) | 18.9 | 20.0 |
| | CV(%) | 12.6 | 5.5 |
| Basis weight | g/m$^2$ | 26.8 | 27.4 |
| Bulk | mm | 0.84 | 0.56 |
| Compression properties | WC(N * m/m$^2$) | 0.95 | 0.59 |
| | $T_0$(mm) | 1.23 | 0.89 |
| | $T_m$(mm) | 0.26 | 0.27 |
| Air permeability (thickness direction) | m$^3$/m$^2$/min | 1170 | 530 |
| Air permeability (planar direction) | m$^3$/m$^2$/min | 50 | 18 |
| Liquid permeability | Liquid permeation time (sec) | 17 | 28 |

Example 6

A spunbond nonwoven fabric 4 was prepared. The spunbond nonwoven fabric 4 was composed of core-sheath composite fibers having a core made of polypropylene and a sheath made of ethylene/propylene copolymer. Bonded sections 7 were situated as embossing on the spunbond nonwoven fabric 4, as shown in FIG. 10. The property values of the spunbond nonwoven fabric 4 are shown in Table 4.

A nonwoven fabric 9 was obtained in the same manner as Example 5, except that the spunbond nonwoven fabric 3 was changed to the spunbond nonwoven fabric 4. The property values of the nonwoven fabric 9 are shown in Table 4.

Comparative Example 4

A nonwoven fabric 10 was obtained in the same manner as Example 6, except that the spunbond nonwoven fabric 4 was subjected directly to steam treatment without passing through a gear stretching step. The property values of the nonwoven fabric 10 are shown in Table 4.

TABLE 4

| | | Example No. | |
|---|---|---|---|
| | | Example 6 | Comp. Ex. 4 |
| | | Nonwoven fabric No. | |
| | | Nonwoven fabric 9 | Nonwoven fabric 10 |
| Initial properties | | | |
| Fibers | Diameter (μm) | | 18.9 |
| | CV(%) | | 7.1 |
| Basis weight | g/m$^2$ | | 45.9 |
| Bulk | mm | | 0.38 |
| Compression properties | WC(N * m/m$^2$) | | 0.19 |
| | $T_0$(mm) | | 0.47 |
| | $T_m$(mm) | | 0.26 |
| Air permeability (thickness direction) | m$^3$/m$^2$/min | | 110 |
| Air permeability (planar direction) | m$^3$/m$^2$/min | | 1.5 |
| Liquid permeability | Liquid permeation time (sec) | | 20 |
| Properties after gear stretching | | | |
| Basis weight | g/m$^2$ | 39.5 | |
| Bulk | mm | 1.06 | |
| Compression properties | WC(N * m/m$^2$) | 1.66 | |
| | $T_0$(mm) | 1.59 | |
| | $T_m$(mm) | 0.47 | |
| Air permeability (thickness direction) | m$^3$/m$^2$/min | 490 | |
| Air permeability (planar direction) | m$^3$/m$^2$/min | 35 | |
| Properties have steam treatment | | | |
| Fibers | Diameter (μm) | 17.2 | 18.9 |
| | CV(%) | 14.4 | 7.1 |
| Basis weight | g/m$^2$ | 42.2 | 46.4 |
| Bulk | mm | 0.87 | 0.66 |
| Compression properties | WC(N * m/m$^2$) | 0.96 | 0.60 |
| | $T_0$(ram) | 1.34 | 0.99 |
| | $T_m$(mm) | 0.44 | 0.37 |
| Air permeability (thickness direction) | m$^3$/m$^2$/min | 580 | 310 |
| Air permeability (planar direction) | m$^3$/m$^2$/min | 44 | 17 |
| Liquid permeability | Liquid permeation time (sec) | 1 | 4 |

The nonwoven fabrics formed in Examples 1-6 had larger WC values than the nonwoven fabrics formed in the corresponding comparative examples, and they were therefore more easily deformed with smaller force, while their larger $T_m$ values rendered them more resistant to collapse.

The nonwoven fabrics formed in Examples 1-6 also had higher air permeability in the planar direction, compared to the nonwoven fabrics formed in the corresponding comparative examples.

Specifically, the present disclosure relates to the following aspects.

[Aspect 1]

A nonwoven fabric comprising continuous fibers and bonded sections formed by bonding multiple fibers including the continuous fibers, wherein the nonwoven fabric comprises a first side and a second side on the side opposite the first side, the first side comprises a plurality of projections ($V_{11}$), each projection ($V_{11}$) including at least one bonded section, a plurality of projections ($V_{12}$) including no bonded section, and at least one recess ($C_{11}$), the second side comprises a plurality of recesses ($C_{21}$), each recess ($C_{21}$) overlapping with at least a part of the projection ($V_{11}$) of the first side, and the coefficient of variation of the diameters of the continuous fibers is at least 10%.

[Aspect 2]

The nonwoven fabric according to aspect 1, wherein the second side does not comprise recesses overlapping the projections ($V_{12}$) of the first side.

[Aspect 3]

The nonwoven fabric according to aspect 1 or 2, wherein the second side further comprises a plurality of projections ($V_{21}$) and a plurality of recesses ($C_{22}$) which do not overlap with the projections ($V_{11}$) of the first side.

[Aspect 4]

The nonwoven fabric according to any one of aspects 1 to 3, the nonwoven fabric has one or more open holes that connect one or more recesses ($C_{11}$) of the first side and one or more recesses ($C_{22}$) of the second side.

[Aspect 5]

The nonwoven fabric according to any one of aspects 1 to 4, wherein the continuous fibers have a plurality of necks with partially narrowed diameters.

[Aspect 6]

A nonwoven fabric formed by non-homogeneous stretching of a spunbond nonwoven fabric or meltblown nonwoven fabric comprising continuous fibers and bonded sections, which are formed by bonding between multiple fibers including the continuous fibers, so that a nonwoven fabric having high-stretch regions and low-stretch regions is formed, placing the nonwoven fabric having high-stretch regions and low-stretch regions on a support, and spraying a fluid onto the nonwoven fabric having high-stretch regions and low-stretch regions.

[Aspect 7]

An absorbent article comprising a liquid-permeable top sheet, a liquid-impermeable back sheet and an absorbent core between the liquid-permeable top sheet and liquid-impermeable back sheet, wherein the liquid-permeable top sheet is a nonwoven fabric according to any one of aspects 1 to 6.

[Aspect 8]

A method of forming the nonwoven fabric according to any one of aspects 1 to 6, comprising the steps of, providing a nonwoven fabric comprising continuous fibers and bonded sections formed by bonding multiple fibers including the continuous fibers, non-homogeneous stretching the nonwoven fabric comprising continuous fibers and bonded sections formed by bonding multiple fibers including the continuous fibers, so that a nonwoven fabric having high-stretch regions and low-stretch regions is formed, and placing the nonwoven fabric having high-stretch regions and low-stretch regions on a support and spraying a fluid onto the nonwoven fabric having high-stretch regions and low-stretch regions, so that the nonwoven fabric according to any one of aspects 1 to 6 is formed.

[Aspect 9]

The method according to aspect 8, wherein the support has protrusions and depressions with predetermined shapes and arrangement on the side in contact with the nonwoven fabric.

[Aspect 10]

The method according to aspect 8 or 9, wherein the fluid is heated air, saturated steam or superheated steam.

[Aspect 11]

The method according to any one of aspects 8 to 10, wherein the nonwoven fabric comprising continuous fibers and bonded sections formed by bonding the multiple fibers including the continuous fibers is a spunbond nonwoven fabric or meltblown nonwoven fabric.

REFERENCES SIGNS LIST

1 First side
2 Second side
3 Projection ($V_{11}$)
4 Projection ($V_{12}$)
5 Recess ($C_{11}$)
6 Open hole
7 Bonded section
8 Recess ($C_{21}$)
9 Neck section
11 Gear stretcher
12,12' Gear rolls
13,13' Peripheral surfaces
14,14' Teeth
15 Nonwoven fabric comprising continuous fibers and bonded sections formed by bonding multiple fibers including the continuous fibers.
16 Nonwoven fabric having high-stretch regions and low-stretch regions
17 Gear pitch
18 Gear tooth cutting depth
19 Support
20 Protrusion
21 Depression
22 Fluid nozzle
23 Nonwoven fabric with specific form and specific coefficient of variation
A Machine direction
B Cross direction perpendicular to machine direction

The invention claimed is:

1. A nonwoven fabric comprising continuous fibers and bonded sections formed by bonding multiple fibers including the continuous fibers, wherein the nonwoven fabric comprises a first side and a second side on the side opposite the first side, the first side comprises a plurality of projections (V11), each projection (V11) including at least one bonded section, a plurality of projections (V12) including no bonded section, and at least one recess (C11), the second side comprises a plurality of recesses (C21), each recess (C21) overlapping with at least a part of the projection (V11) of the first side, said projections (V11; V12) and said recesses (C11; C12) are formed by spraying a fluid onto the nonwoven fabric after the nonwoven fabric has been non-homogeneous stretched, the nonwoven fabric has high-stretch regions and low-stretch regions formed by the non-homogeneous stretching wherein sections in which the fiber sizes are relatively thick and sections in which the fiber sizes are relatively thin are mixed among the continuous fibers in the nonwoven fabric, and the coefficient of variation of the diameters of the continuous fibers is at least 10%, and the continuous fibers have a plurality of neck portions with partially narrowed diameters.

2. The nonwoven fabric according to claim 1, wherein the second side comprises no recess overlapping the projection (V12) of the first side.

3. The nonwoven fabric according to claim 1, wherein the second side further comprises a plurality of projections (V21) and a plurality of recesses (C22) which do not overlap with the projections (V11) of the first side.

4. The nonwoven fabric according to claim 1, the nonwoven fabric has one or more open holes that connect one or more recesses (C11) of the first side and one or more recesses (C22) of the second side.

5. An absorbent article comprising a liquid-permeable top sheet, a liquid-impermeable back sheet and an absorbent core between the liquid-permeable top sheet and liquid-impermeable back sheet, wherein the liquid-permeable top sheet is a nonwoven fabric according to claim 1.

* * * * *